United States Patent [19]

Sandsdalen

[11] Patent Number: 4,775,363
[45] Date of Patent: Oct. 4, 1988

[54] ARRANGEMENT IN INJECTION SYRINGE FOR USE ONCE ONLY

[76] Inventor: Christian Sandsdalen, Oppegårdsveien 201, N-1405 Langhus, Norway

[21] Appl. No.: 801

[22] Filed: Jan. 6, 1987

[30] Foreign Application Priority Data

Jan. 7, 1986 [NO] Norway ................................. 860039

[51] Int. Cl.$^4$ ............................................. A61M 5/00
[52] U.S. Cl. ..................................... 604/110; 604/228
[58] Field of Search ................ 604/110, 111, 218, 228

[56] References Cited

U.S. PATENT DOCUMENTS

| 4,367,738 | 1/1983 | Legendre et al. | 604/218 |
| 4,391,272 | 7/1983 | Staempfli | 604/110 |
| 4,493,703 | 1/1985 | Butterfield | 604/110 |

Primary Examiner—John D. Yasko
Attorney, Agent, or Firm—Bell, Seltzer, Park & Gibson

[57] ABSTRACT

In an injection syringe for use once only the piston rod (4) is connected to the piston (3) by claws (9) which upon pressing of the piston rod (4) against the piston (3) during injection break or become deformed to such an extent that it is no longer possible to retract the piston (3) for the purpose of refilling the syringe. The deformation is effected by means of a conical portion (13) on the piston, said portion by wedge effect pressing the claws (9) radially outwardly when the piston rod (4) is pressed against the piston (3). The rigidity and strength of the claws (9) is adapted to the resistance experienced during injection of a liquid so that the claws will certainly be broken or otherwise brought out of engagement with the piston (11). On the other hand the force required to push the piston forward in an empty syringe does not have to be sufficient to break the claws (9).

9 Claims, 1 Drawing Sheet

U.S. Patent  Oct. 4, 1988  4,775,363
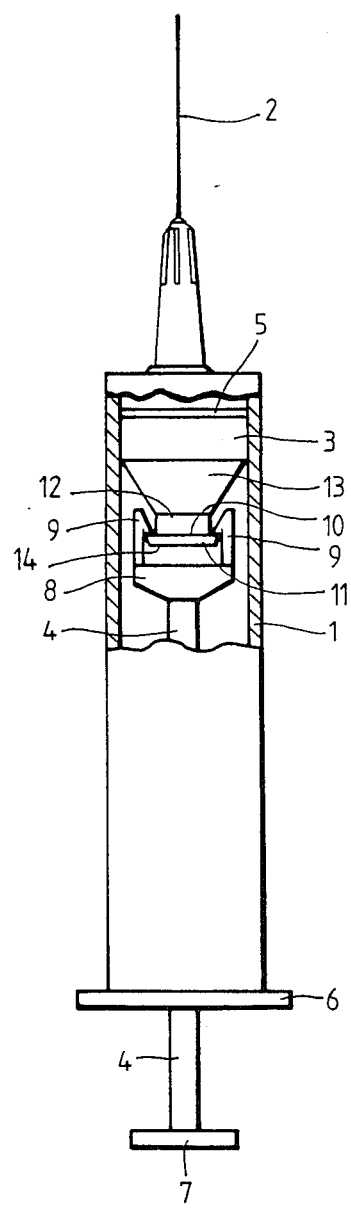

ARRANGEMENT IN INJECTION SYRINGE FOR USE ONCE ONLY

The invention relates to an arrangement in an injection syringe for use once only, comprising a cylinder and a piston having a piston rod.

For hygienic reasons it is desirable that injection syringes are not used more than once, and in recent years a simple and cheap injection syringe which is intended for use once only has been designed. However, such syringes have nevertheless often been used several times.

The object of the invention is to develope an injection syringe which cannot be used more than once. According to the invention this is achieved in that the piston rod is connected to the piston by means which upon pressing of the piston rod against the piston during injection break or become deformed to such an extent that it is no longer possible to retract the piston for the purpose of refilling the syringe. Thus, the connection between the piston rod and the piston shall be such as to allow the piston to be retracted for filling the syringe once and then to be made ineffective when the piston rod is pressed against the piston during injection. The piston can still be pressed for injection of the liquid to be injected, since this only requires the piston rod to abut the end of the piston. The connection between the piston rod and the piston can be so designed that the pulling connection is not made ineffective upon pressing of the piston when the syringe is empty, since a force which is larger than the resistance to pushing the piston forward when the syringe is empty can be required between the piston and the piston rod to make the pulling connection ineffective. It is sufficient if the pulling connection is made ineffective when the piston is pushed forward against the resistance provided by the cannula and the body tissue into which the liquid is to be injected. For some purposes including intravenous injection it is even possible to provide for the pulling connection not to become inaffective until an aspiration into the syringe has been effected.

According to a preferred embodiment the end of the piston rod may carry one or more claws which engage an undercut surface on the piston, and the piston may have inclined surfaces against which the claws will bear when the piston rod is pressed, and which therefore by wedge effect deform the claws or break them away. If the means connecting the piston and the piston rod are integral with both these elements, it is, of course, necessary to cause a complete breaking of these means, whereas in other cases it will be sufficient to effect a deformation disconnecting the piston rod and the piston.

Preferably a claw is provided at each of the outer ends of a yoke at the end of the piston rod. The inclined surfaces with which the claws cooperate may suitably be formed by a conical portion at the rear end of the piston.

The undercut surface may be formed by the forwardly facing side of a collar at the narrow end of the conical portion.

To facilitate breaking of the claws the base thereof may have an incision governing the place of rupture. The claws should be made of a material which is sufficiently brittle to cause complete breaking of the claws away from the piston rod due to the said wedge effect.

It will be understood that the claws can be provided on the piston instead of on the piston rod, whereas the undercut surface engaged by the claws can be provided on the piston rod instead of on the piston.

The invention will now be described in more detail, reference being made to the drawing which—partly in section—illustrates a diagrammatical view of an injection syringe incorporating an arrangement according to the invention.

In the drawing 1 designates a cylinder having a cannula 2, whereas 3 designates a piston having a piston rod 4 and an annular gasket 5 sealing against the cylinder 1. The rear end of the cylinder 1 is sealed by an end wall 6 extending beyond the peripheral walls of the cylinder 1 in the usual manner. Of course, the piston rod 4 extends through the end wall 6 and is at the end shaped with a handle 7.

So far the structure of the described injection syringe is conventional. The novel features according to the invention relate to the connection between the piston 3 and the piston rod 4. As will be seen the piston rod 4 carries a yoke 8 which at each end has a claw 9 which engages the forwardly facing side 10 of a collar 11 on the piston 3. The collar 11 is provided at the end of a short cylindrical portion 12 which through a conical portion 13 is connected with the portion of the piston 3 sealing against the walls of the cylinder 1.

As shown in the drawing there is a small clearance between the free end of the claws 9 and the surface of the conical portion 13, and this distance is substantially less than the distance between the end surface 14 of the piston 3 and the yoke 8.

The function of the illustrated injection syringe is as follows:

When the syringe is supplied the piston will be in the fully advanced position, as shown in the drawing. When the cannula 2 has been inserted into an ampoule or similar container for a liquid to be injected, the piston rod 4 is retracted and carries with it the piston 3 by means of the claws 9 and the rear side 10 of the collar 11. The syringe is thus filled. When the syringe has been filled and is subsequently pushed forward for injection of the liquid the claws 9 will abut the conical portion 13. Due to the resistance provided by the cannula 2 and possibly by the surrounding tissue (or the blood in a vein) during injection the claws 9 will be pressed with a not insignificant force against the conical portion 13. As a consequence of the wedge effect of the conical portion 13 the claws will thus be forced radially outwards. Due to the fact that the claws at the base thereof have an incision (not illustrated) governing the place of rupture or has otherwise been given a relatively small section, and due to the fact that they are made of a material which is relatively brittle, they will easily be broken away and thereby make the pulling connection between the piston rod 4 and the piston 3 ineffective. The piston 3 can still be pushed forward for injection of the liquid, since the yoke 8 will abut the end surface 14 of the piston 3. However, when the injection has been completed the piston 3 can no longer be retracted for refilling of the syringe.

It is, of course, not necessary to break off the claws 9 completely. It is sufficient to deform them to such an extent that they do not engage the collar 11.

Also various other modifications of the invention will be readily apparent to those skilled in the art. Thus, it will not be difficult to design connection means which may, for instance, be integral with the piston rod 4 as well as the piston 3, but which break the first time the piston rod 4 is pressed against the piston 3, at least when the syringe is filled and therefore provides a substantial resistance to the movement of the piston.

In syringes which are especially intended for use in hospitals, it is desirable to allow for aspiration to be effected, e.g. for use in intravenous injection. This can be obtained by providing for the pulling connection only to be made ineffective subsequent to the aspiration, e.g. by using a somewhat less brittle or fragile material or a smaller incision or a collar farther up on the conical portion of the piston.

I claim:

1. A disposable, non-reusable injection syringe comprising
    a tubular cylinder having an internal cylindrical bore, and with said cylinder defining a forward discharge end and an opposite rear end,
    a piston slideably mounted in said bore of said cylinder,
    a rod extending through said rear end of said cylinder and having one end positioned adjacent said piston, and
    cooperating surface means mounted on said one end of said rod and said piston for interconnecting said rod and piston so as to permit the same to be withdrawn together in a rearward direction to aspirate a liquid into said bore of said cylinder through said forward discharge end of said cylinder and for causing said rod and piston to be permanently disconnected from each other upon said rod and piston being moved forwardly against the resisting force applied to the piston when the aspirated fluid is injected forwardly through said forward discharge end, to thereby prevent a further aspiration of a liquid into said cylinder.

2. The syringe as defined in claim 1 wherein said cooperating surface means comprises an undercut surface mounted on one of said forward end of said rod and said piston, with said undercut surface facing in a first axial direction, and a pair of axially extending claws mounted on the other of said forward end of said rod and said piston, and wtih said pair of claws each including an axially facing shoulder opposing said undercut surface and so that the shoulders of said claws and said undercut surface engage each other during rearward withdrawal of said rod and piston.

3. The syringe as defined in claim 2 wherein said one of said forward end of said rod and said piston further includes a wedge-shaped surface positioned adjacent said undercut surface, and such that during forward movement of said rod and piston said claws engage said wedge-shaped surface and are laterally spread apart.

4. The syringe as defined in claim 3 wherein said claws are constructed so as to be adapted to break upon being laterally spread apart by their engagement with said wedge-shaped surface during forward movement of said rod and piston.

5. The syringe as defined in claim 3 wherein said claws are constructed of a material adapted to be permanently deformed upon being laterally spread apart by their engagement with said wedge-shaped surface during forward movement of said rod and piston.

6. The syringe as defined in claim 1 wherein said cooperating surface means comprises
    first surface means mounted on said piston and which includes a rearwardly facing end surface, a forwardly facing undercut surface positioned forwardly of said end surface, and a rearwardly facing wedge-shaped surface positioned forwardly of said undercut surface, and
    second surface means mounted on said one end of said rod and which includes a forwardly facing end surface and a pair of laterally spaced apart and forwardly extending claws, and with said pair of claws each including a rearwardly facing shoulder positioned to oppose and engage said undercut surface of said first surface means so that the shoulders of said claws and said undercut surface engage each other during rearward withdrawal of said rod and piston.

7. The syringe as defined in claim 6 wherein said claws extend forwardly a distance sufficient to engage said wedge-shaped surface and be spread apart thereby prior to the engagement of said forwardly facing end surface with said rearwardly facing end surface during the forward movement of the rod and piston.

8. The syringe as defined in claim 7 wherein said bore of said cylinder is substantially smooth and uninterrupted along its length.

9. The syringe as defined in claim 8 further comprising a hypodermic cannula mounted to said forward end of said cylinder.

* * * * *